(12) United States Patent
Govari et al.

(10) Patent No.: US 11,819,634 B2
(45) Date of Patent: Nov. 21, 2023

(54) ROBOTIC ASSISTER FOR CATHETER INSERTION

(71) Applicant: BIOSENSE WEBSTER (ISRAEL) LTD., Yokneam (IL)

(72) Inventors: Assaf Govari, Haifa (IL); Christopher Thomas Beeckler, Brea, CA (US)

(73) Assignee: Biosense Webster (Israel), Ltd., Yokneam (IL)

( * ) Notice: Subject to any disclaimer, the term of this patent is extended or adjusted under 35 U.S.C. 154(b) by 181 days.

(21) Appl. No.: 17/458,742

(22) Filed: Aug. 27, 2021

(65) Prior Publication Data

US 2021/0386970 A1    Dec. 16, 2021

Related U.S. Application Data

(62) Division of application No. 14/090,579, filed on Nov. 26, 2013, now Pat. No. 11,129,962.

(51) Int. Cl.
| | |
|---|---|
| *A61M 25/01* | (2006.01) |
| *A61B 34/20* | (2016.01) |
| *A61B 34/30* | (2016.01) |
| *A61B 17/00* | (2006.01) |

(52) U.S. Cl.
CPC ......... *A61M 25/0122* (2013.01); *A61B 34/20* (2016.02); *A61B 34/30* (2016.02); *A61M 25/0127* (2013.01); *A61M 25/0155* (2013.01); *A61B 2017/00539* (2013.01); *A61B 2017/00544* (2013.01); *A61B 2034/2051* (2016.02); *A61B 2034/301* (2016.02); *A61M 25/0116* (2013.01)

(58) Field of Classification Search
CPC ............... A61B 34/30; A61M 25/0116; A61M 25/0122; A61M 25/0155
See application file for complete search history.

(56) References Cited

U.S. PATENT DOCUMENTS

| 5,391,199 A | 2/1995 | Ben-Haim |
|---|---|---|
| 7,214,230 B2 | 5/2007 | Brock |
| 2002/0004731 A1 | 1/2002 | Dawson |

(Continued)

FOREIGN PATENT DOCUMENTS

| CN | 102655802 A | 9/2012 |
|---|---|---|
| WO | 99/45994 | 9/1999 |

(Continued)

OTHER PUBLICATIONS

U.S. Appl. No. 12/539,707, filed Aug. 12, 2009.

*Primary Examiner* — Diane D Yabut (57) ABSTRACT

Apparatus for controlling motion of an invasive probe relative to a sheath enclosing the probe. The apparatus includes an outer casing, configured for connection to the sheath. The apparatus further includes a drive mechanism, fixedly connected to the outer casing. The drive mechanism has a first set of components, configured to translate the probe along a direction parallel to as axis of the probe, in order to advance and retract the probe with respect to the sheath in a translational stepwise manner. The drive mechanism also includes a second set of components, configured to rotate the probe around the axis of the probe, in order to rotate the probe clockwise and counter-clockwise, with respect to the sheath, in a rotational stepwise manner.

13 Claims, 8 Drawing Sheets

(56) References Cited

U.S. PATENT DOCUMENTS

| | | | |
|---|---|---|---|
| 2002/0047317 A1* | 4/2002 | Dawson | H02K 41/03 |
| | | | 310/12.14 |
| 2005/0020338 A1 | 9/2005 | Govari et al. | |
| 2009/0082722 A1 | 3/2009 | Munger | |
| 2010/0006983 A1 | 1/2010 | Wenderow | |
| 2010/0069833 A1* | 3/2010 | Wenderow | A61M 25/0147 |
| | | | 604/95.01 |
| 2010/0175701 A1* | 7/2010 | Reis | A61B 90/40 |
| | | | 74/461 |
| 2012/0279325 A1 | 11/2012 | Rodriguez Y Baena et al. | |
| 2013/0123802 A1 | 5/2013 | Comber | |
| 2013/0172814 A1* | 7/2013 | Olson | A61M 25/0147 |
| | | | 604/95.04 |
| 2014/0027638 A1 | 1/2014 | Walker | |
| 2014/0276389 A1* | 9/2014 | Walker | A61B 34/30 |
| | | | 604/95.01 |
| 2014/0277747 A1* | 9/2014 | Walker | A61B 34/30 |
| | | | 700/275 |

FOREIGN PATENT DOCUMENTS

| | | |
|---|---|---|
| WO | 2007/098494 A1 | 8/2007 |
| WO | 2012/037506 A2 | 3/2012 |

* cited by examiner

ROBOTIC ASSISTER FOR CATHETER INSERTION

CROSS-REFERENCE TO RELATED APPLICATIONS

This application is a divisional of U.S. patent application Ser. No. 14/090,579 filed on Nov. 26, 2013, the disclosures of all of which are hereby incorporated by reference as if set forth in their entirety herein.

FIELD OF THE INVENTION

The present invention relates generally to invasive medical instruments, and specifically to methods and apparatus for manipulating and steering an invasive probe for diagnostic or therapeutic purposes.

BACKGROUND OF THE INVENTION

Various types of robotic steering mechanisms for catheters are known in the art. For example, U.S. Patent Application Publication 2005/0203382, whose disclosure is incorporated herein by reference, describes a robot for steering a catheter that is designed to be manually manipulated by a user. The catheter has a user-operable control handle or a thumb control, and the robot holds and manipulates the catheter by generally mimicking the motions of a hand of a surgeon.

As another example, PCT International Publication WO 99/45994, whose disclosure is incorporated herein by reference, describes a remote control catheterization system including a propelling device, which controllably inserts a flexible, elongate probe into the body of a patient. A control console, in communication with the propelling device, includes user controls which are operated by a user of the system remote from the patient to control insertion of the probe into the body by the propelling device.

Documents incorporated by reference in the present patent application are to be considered an integral part of the application except that to the extent any terms are defined in these incorporated documents in a manner that conflicts with the definitions made explicitly or the present specification, only the definitions in the present specification should be considered.

SUMMARY OF THE INVENTION

An embodiment of the present invention provides apparatus for controlling motion of an invasive probe relative to a sheath enclosing the probe, the apparatus including:
  an outer casing, configured for connection to the sheath; and
  a drive mechanism, fixedly connected to the outer casing, the drive mechanism including:
  a first set of components, configured to translate the probe along a direction parallel to an axis of the probe, in order to advance and retract the probe with respect to the sheath in a translational stepwise manner; and
  a second set of components, configured to rotate the probe around the axis of the probe, in order to rotate the probe clockwise and counter-clockwise, with respect to the sheath, in a rotational stepwise manner.

Typically, the first set and the second set include a common sub-set of components consisting of first and second grippers, configured to releasably grip the probe first and second positions the first gripper may be fixed relative to the sheath, and the second gripper may be movable relative to the sheath. Typically, the first gripper grips the probe while the second gripper releases the probe and while the first gripper implements one of translation and rotation of the probe.

In a disclosed embodiment the components consist of hydraulic components. The hydraulic components may be configured to be operated by a gas. Alternatively, the hydraulic components may be configured to be operated by a liquid.

In a further disclosed embodiments the components consist of electromagnetic components. The apparatus may include circuitry configured to supply currents to the electromagnetic components on receipt of a control signal.

In a yet further disclosed embodiment the first set consists of a coil and a magnet configured, on energization of the coil, to implement one of advancement and retraction of the probe.

In an alternative embodiment the apparatus includes solenoids configured to open and close first and second grippers in alternation so as to implement one of the translational stepwise manner of translation and the rotational stepwise manner of rotation.

In a further alternative embodiment the second set consists of a coil and a magnet configured, on energization of the coil, to implement one of a clockwise and a counter-clockwise rotation of the probe.

Typically, the invasive probe is used in an invasive procedure on a heart of a subject.

In a yet further alternative embodiment controlling the motion includes multiplying a force applied to the invasive probe.

Alternatively or additionally controlling the motion includes overcoming friction between the sheath and the invasive probe.

There is further provided, according to an embodiment of the present invention a method for controlling motion of an invasive probe relative to a sheath enclosing the probe, including:
  connecting an outer casing to the sheath;
  fixedly connecting a drive mechanism to the outer casing;
  operating a first set of components in the drive mechanism, to translate the probe along a direction parallel to an axis of the probe, is order to advance and retract the probe with respect to the sheath in a translational stepwise manner; and
  operating a second set of components in the drive mechanism to rotate the probe around the axis of the probe, in order to rotate the probe clockwise and counter-clockwise, with respect to the sheath, in a rotational stepwise manner.

The present disclosure will be more fully understood from the following detailed description of the embodiments thereof, taken together with the drawings, in which:

DETAILED DESCRIPTION OF EMBODIMENTS

Overview

An embodiment of the present invention provides an apparatus for controlling motion of an invasive probe relative to a sheath enclosing the probe. Typically the apparatus may be used to overcome the friction that is normally present when the probe moves, in either a translational or a rotational manner, with respect to the sheath. The motion of the probe may be initiated by a robotic drive for the probe.

The apparatus comprises an outer casing which is connected to the sheath, and a drive mechanism which is fixedly connected to the outer casing. The drive mechanism comprises a first set of components which translate the probe along a direction parallel to an axis of the probe, in order to advance and retract the probe with respect to the sheath in a translational stepwise manner. The drive mechanism also comprises a second set of components, which rotate the probe around the axis of the probe, in order to rotate the probe clockwise and counter-clockwise, with respect to the sheath, in a rotational stepwise manner.

Typically, the first set of components and the second set of components comprise a common sub-set of components. The common sub-set comprises a first gripper of the probe and a second gripper of the probe, configured to releasably grip the probe in first and second positions. To accomplish the stepwise motions, the first gripper grips the probe while the second gripper releases it, allowing the first gripper to perform a transitional or rotational motion. The second gripper then grips the probe, and the first gripper releases the probe and returns to its initial position. The actions of alternately gripping and releasing the probe, and moving the probe while the first gripper grips the probe, may be repeated, as necessary, in an iterative manner.

In an alternative embodiment, rather than the apparatus being configured to overcome friction between the probe and the sheath, the apparatus may be configured to multiply the force applied to the probe.

System Description

Figure 1:
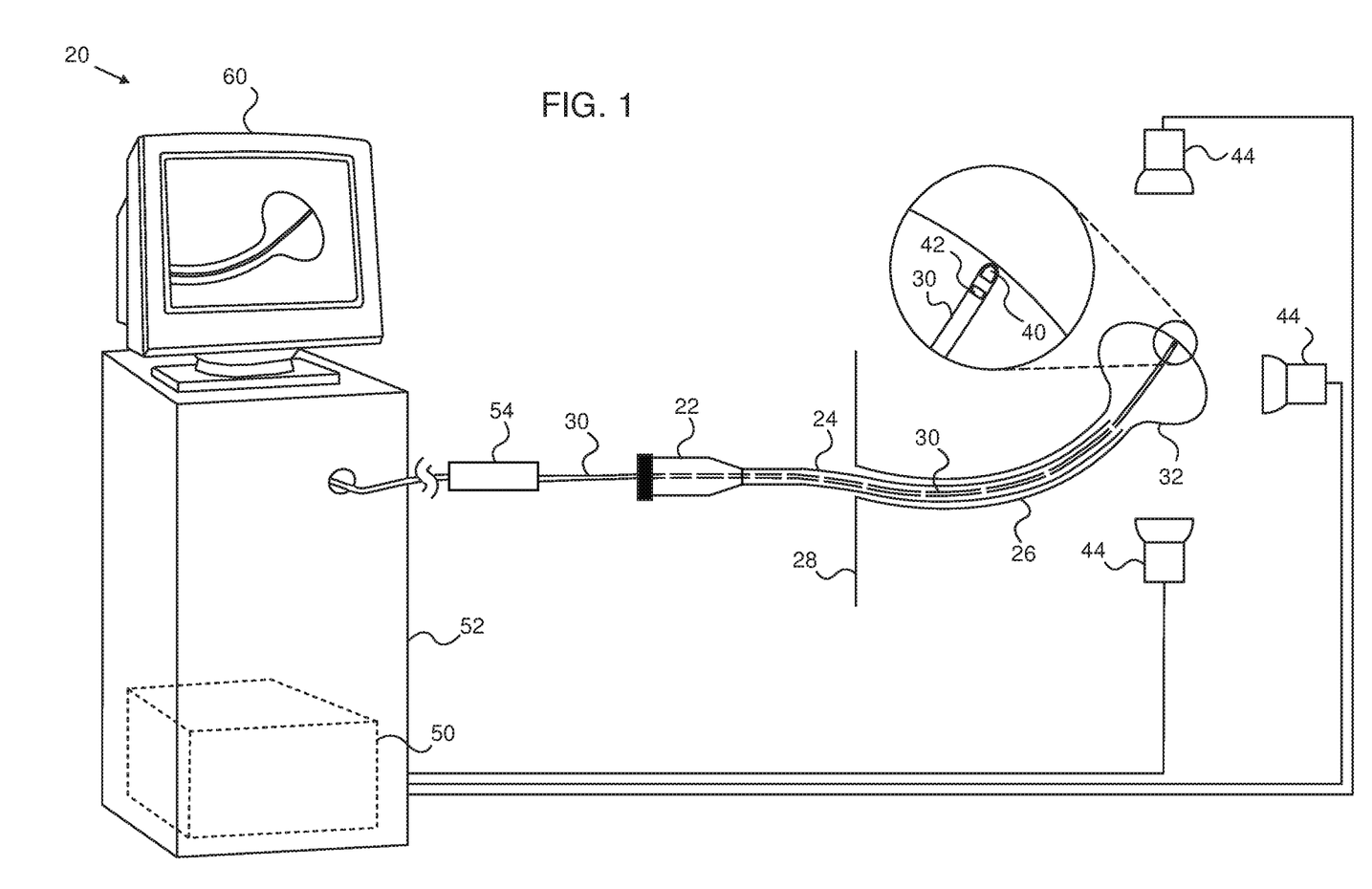
FIG. 1 is a schematic, pictorial illustration of a catheterization system using an automatic catheter motion assister, according to an embodiment of the present invention.

FIG. 1 is a schematic, pictorial illustration of a catheterization system 20 using an automatic catheter motion assister 22, according to an embodiment of the present invention. In the illustrated embodiment, a physician inserts a catheter guiding sheath 24 into a lumen 26 of a subject 28. The lumen permits entry of a catheter 30, also referred to herein as probe 30, into a body cavity 32, such as a chamber of the heart of the subject. For example, in the case of insertion into the heart, lumen 26 may comprise the femoral vein. The distal tip of the catheter (shown enlarged in the inset) typically comprises a functional element 40 for diagnostic and/or therapeutic purposes. For example, element 40 may comprise an electrode for electrical sensing and/or ablation of tissue, or an ultrasonic transducer for intracardiac imaging. Other types of functional elements and invasive probes that may be driven in the manner described below will be apparent to those skilled in the art and are considered to be within the scope of the present invention.

In the pictured embodiment, catheter 30 also comprises a position transducer 42 within its distal tip, for use in determining position coordinates of the tip. For example, transducer 42 may comprise a magnetic field sensor, which detects magnetic fields generated by field transducers 44 at known locations outside the body. Magnetic position sensing systems of this sort are described, for example, in U.S. Pat. No. 5,391,199, whose disclosure is incorporated herein by reference, and are used in intracardiac tracking systems, such as the CARTO™ system (produced by Biosense Webster Inc., Diamond Bar, California). Alternatively, transducer 42 may generate fields to be sensed by transducers 44. Further alternatively or additionally, transducer 42 may comprise any other suitable type of position transducer known in the art, such as an electrode for purposes of impedance-based position sensing, an ultrasonic transducer, or a fiducial mark for locating the catheter tip in a two- or three-dimensional image of the body.

A position-sensing module 50 communicates with transducers 42 and 44 in order to determine the position coordinates of the catheter tip inside the body of the subject. A control unit 52 uses the coordinates to control a robotic drive 54 (described in more detail below with respect to FIG. 2) in order to navigate catheter 30 to desired positions within the body. In this respect, control unit 52 may operate autonomously, in accordance with predefined program instructions. Alternatively or additionally, the control unit may present the catheter position on a display 60, typically juxtaposed on a map or image of cavity 32, so as to enable a human operator (not shown) to control the catheter. Control unit 52 typically comprises a general-purpose computer processor, which is programmed in software to carry out the desired functions.

Robotic drive 54 allows a human operator to automatically make adjustments to catheter 30 using control unit 52. The adjustments typically include advancing and retracting the catheter in lumen 26, along an axis of the catheter, as well as rotating the catheter clockwise or counter-clockwise about its axis. The human operator inputs desired movements of the catheter, typically by manipulation of a pointing device such as a mouse or joystick connected to the control unit, and the control unit converts the pointing device manipulations to relevant signals to robotic drive 54.

Figure 2:
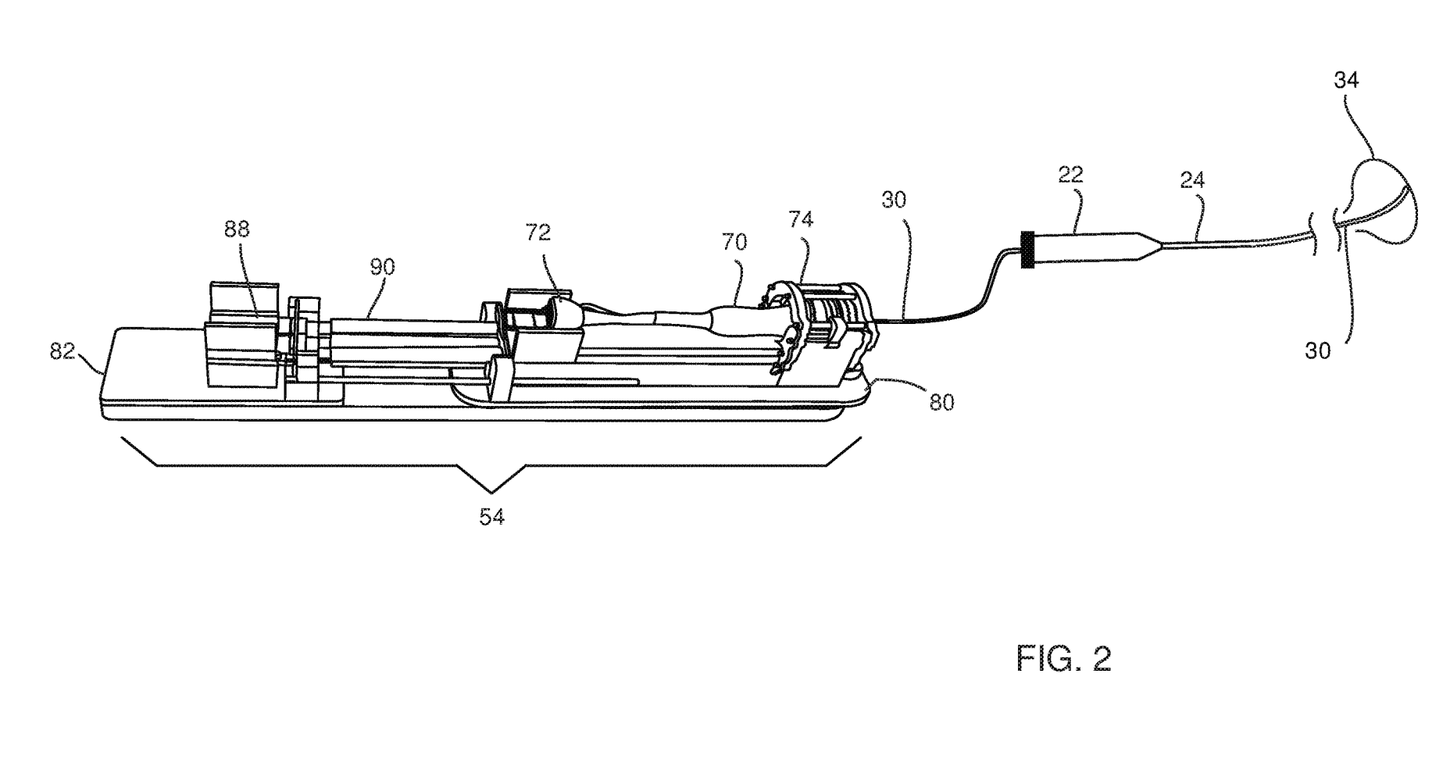
FIG. 2 is a schematic, pictorial illustration showing a catheter held in a robotic drive, according to as embodiment of the present invention.

FIG. 2 is a schematic, pictorial illustration showing catheter 30 held in robotic drive 54, according to an embodiment of the present invention. Catheter 30 comprises a handle 70, which is designed to be held and manipulated by a human operator. In conventional use, the operator inserts sheath 24 percutaneously into lumen 26, and inserts the distal end of the catheter into the sheath. The operator then advances the catheter, through sheath 24, along its longitudinal axis into cavity 32. The operator moves the handle back and forth in order to retract and advance the catheter, and may also rotate the handle about the axis in order to rotate the catheter itself. A proximal terminal 72 connects the catheter to control unit 52, but the connection to the terminal is omitted from FIG. 2 for the sake of simplicity and clarity of illustration.

In embodiments of the present embodiment, however, drive 54 may carry out these manipulations instead of the human operator. A jig 74 holds handle 70. The jig comprises gearing for rotating the handle about the axis. Jig 74 is mounted on a platform 80, which is capable of translating relative to a base 82 in order to advance and retract the catheter along its axis. A drive module 88 is coupled by a transmission 90 to jig 74 in order to rotate the gearing and to translate platform 46 along base 47. A pointing device such as a joystick may be connected to control unit 52, and the operator of system 20 may use the pointing device to cause the control unit to generate appropriate signals for drive module 88.

A more detailed description of a drive similar to drive 54 is provided in U.S. patent application Ser. No. 12/539,707, which is incorporated herein by reference.

As illustrated in FIG. 2, catheter 30 exits from handle 70, and enters into assister 22. Assister 22 connects to sheath 24, and catheter 30 then traverses the assister and the sheath, and enters into cavity 34.

Figure 3:
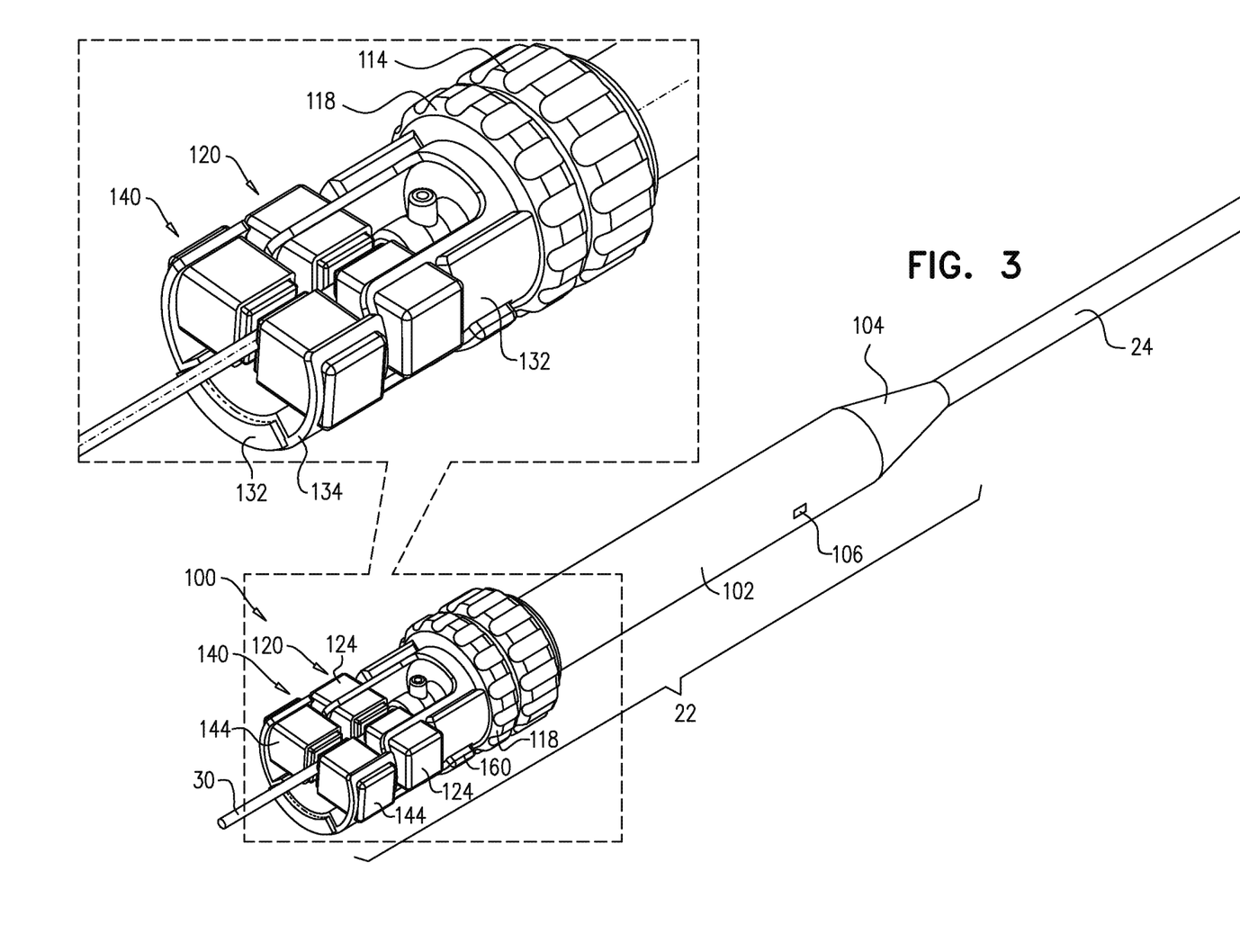
FIG. 3 is a schematic diagram of an assister in an assembled state, according to an alternative embodiment of the present invention.
Figure 4:
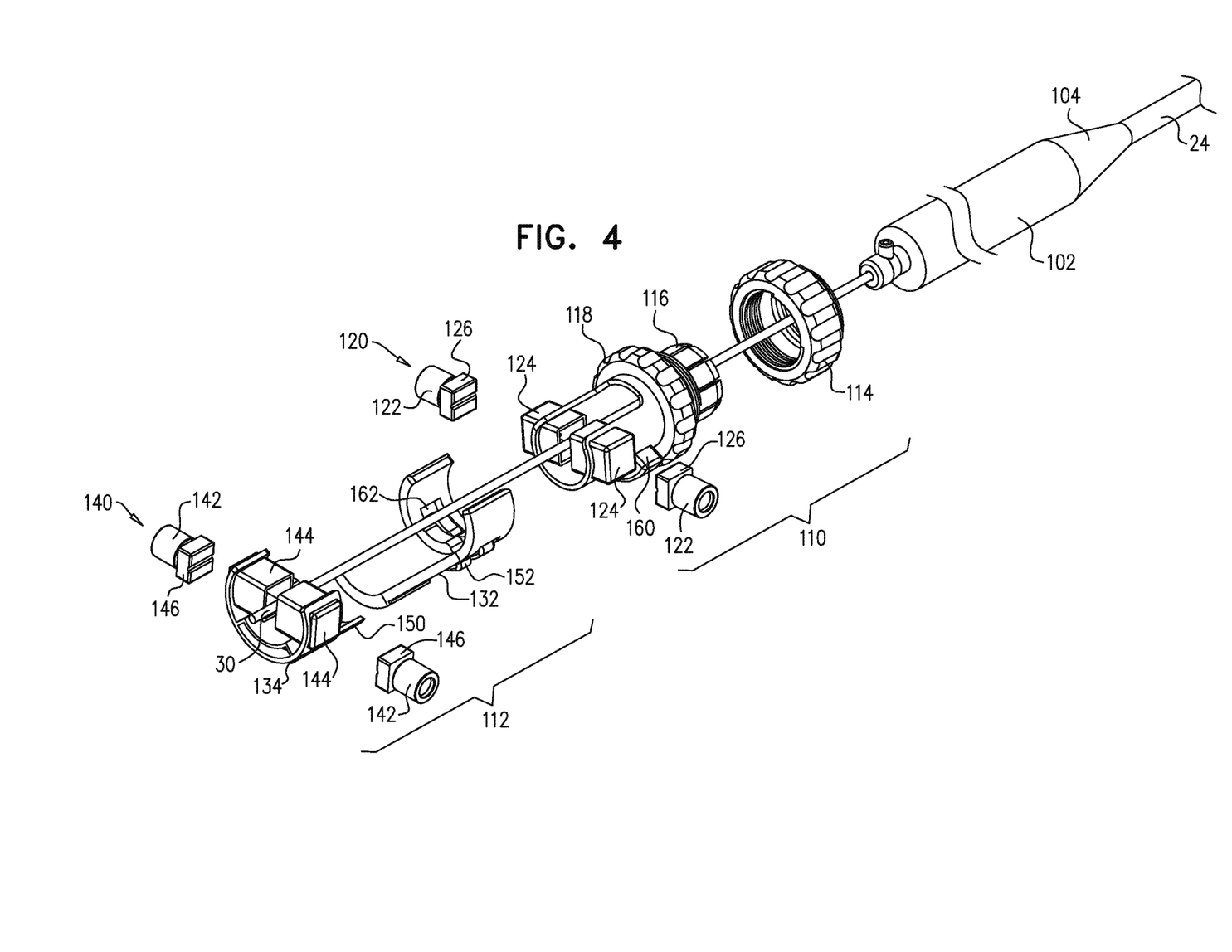
FIG. 4 is a schematic exploded diagram of the assister, according to an embodiment of the present invention.

FIG. 3 is a schematic diagram of assister 22 in an assembled state, and FIG. 4 is a schematic exploded diagram of the assister, according to an embodiment of the present invention. Assister 22 comprises a drive module 100, which catheter 30 enters, and a cylindrical outer casing 102 which fixedly connects via a transition region 104 to sheath 24. Catheter 30 traverses drive module 100, outer casing 102, and transition region 104, and enters sheath 24. Elements of module 100 are driven by currents generated in circuitry 106, typically an ASIC (application specific integrated circuit), which in response to a control signal from control unit 52 generates the required currents. By way of example circuitry 106 is assumed to be installed in casing 102, but circulatory 106 may be installed in any other convenient location, including within control unit 52, and connected via a cable to the driven elements so as to provide the required currents.

Drive module 100 comprises a fixed unit 110, and a movable unit 112. As described in more detail below, movable unit 112 may move in a direction defined by an axis of catheter 30, as well as in a direction around the axis, both motions being with respect to fixed unit 110. The former motion is herein also termed parallel or translational motion, and the latter motion is herein also termed rotational motion. Unit 110 may be fixed with respect to casing 102, and so with respect to sheath 24, by means of a locking ring 114. Fixed unit 110 comprises a collet 116 which is connected to a fixed unit base section 118 of the fixed unit, and the unit may be fixed to casing 102 by screwing the locking ring onto the collet. The following description assumes that unit 110 has been fixed to casing 102 by means of the locking ring and the collet.

Fixed unit base section 118 comprises a fixed gripper 120, which, on activation, grips catheter 30. Gripper 120 comprises a pair of opposing solenoids 122 which are housed in respective retaining enclosures 124 of base section 118. Respective jaws 126 are held by solenoids 122, and, when the solenoids are energized, engage and hold the catheter, so that the catheter is fixed with respect to sheath 24. If the solenoids are not energized, jaws 126 do not engage the catheter, and so allow the catheter to move freely with respect to the sheath.

Movable unit 112 comprises two sub-sections 132 and 134, the two sections being configured to mate with each other and to also move in a limited sliding manner with respect to each other a parallel motion direction, i.e., parallel to an axis defined by catheter 30. Sub-section 134 comprises a movable gripper 140, which is generally similar to gripper 120 described above. Thus gripper 140 comprises a pair of opposing solenoids 142 which are housed in respective retaining enclosures 144 of sub-section 134. Respective jaws 146 are held by solenoids 142, and, when the solenoids are energized, engage and hold the catheter so that sub-section 134 holds the catheter. When solenoids 142 are not energized, the catheter is free to move with respect to sub-section 134.

The parallel sliding, or translational, motion of sub-section 134 with respect to sub-section 132 is configured to be limited in both a distal and a proximal direction. Thus, for example, a surface 150 of sub-section 134 contacting a stop 152 of sub-section 132 limits motion of sub-section 134 in a distal direction. A typical range for the translational motion of sub-section 134, i.e., from a distal limit to a proximal limit, is approximately 2 mm.

When fixed unit 110 and movable unit 112 are assembled together, a retaining protrusion 160 in fixed unit 110 mates with a slot 162 in movable unit 112. Slot 162 is larger, as measured in a direction around catheter 30, than protrusion 160 so that movable unit 112 is able to move in a rotational motion, i.e., in a direction around an axis defined by catheter 30. The rotational motion is limited by the difference in dimensions of protrusion 160 and slot 162. A typical overall range for the rotational motion of movable unit 112 is approximately 5°.

In addition to the electromagnetic components described above, comprised in fixed unit 110 and movable unit 112, for gripping catheter 30, units 110 and 112 comprise further electromagnetic components which are configured to provide the respective forces required for the translational and rotational motions referred to above.

Figure 5:
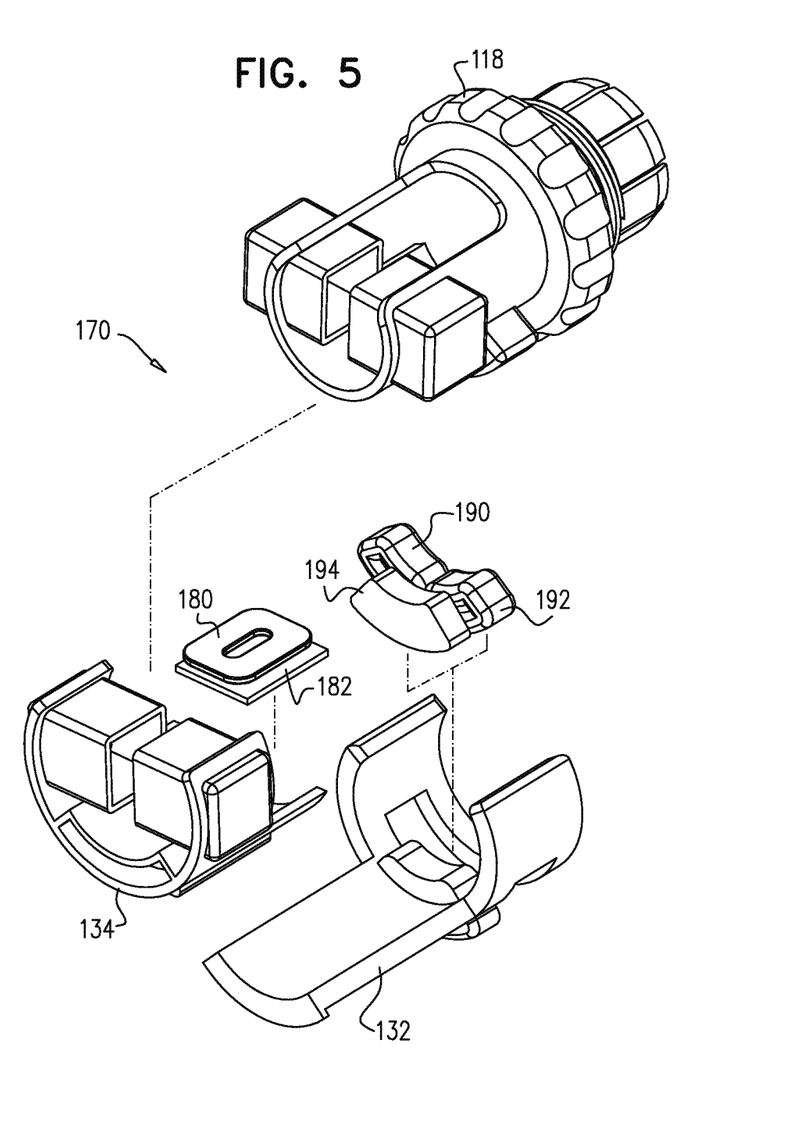
FIG. 5 is a schematic exploded diagram illustrating electromagnetic components of the assister providing translational and rotational forces, according to as embodiment of the present invention.

FIG. 5 is a schematic exploded diagram illustrating electromagnetic components of assister 22 providing translational and rotational forces, according to an embodiment of the present invention.

For simplicity and clarity, only the electromagnetic components, also referred to herein as force electromagnetic components 170, of assister 22 providing the translational and rotational forces, and their retaining elements, are shown in FIG. 5. The translational force for assister 22 is provided by a coil 180, which, when energized, interacts with a permanent magnet 182. Coil 180 is retained in sub-section 132, and magnet 182 is held in sub-section 134. The rotational force for assister 22 is provided by coils 190 and 192, when energized, interacting with a permanent magnet 194. Coils 190 and 192 are retained in fixed base unit section 118, and magnet 194 is held in sub-section 132. It will be understood that the electromagnetic components described above allow the translational and rotational forces to be implemented completely independently of each other. Thus only a translational force, or only a rotational force, or both a translational and a rotational force, may be applied by electromagnetic components 170, and the type of force that is applied depends on which of coils 180, 190, and/or 192 is energized.

Embodiments of the present invention use the electromagnetic components described above to move the catheter with respect to the sheath in either a translational direction parallel to an axis defined by the catheter, or in a rotational direction around the axis, or in both directions. The motion for all of these cases is implemented in a stepwise manner.

Figure 6:
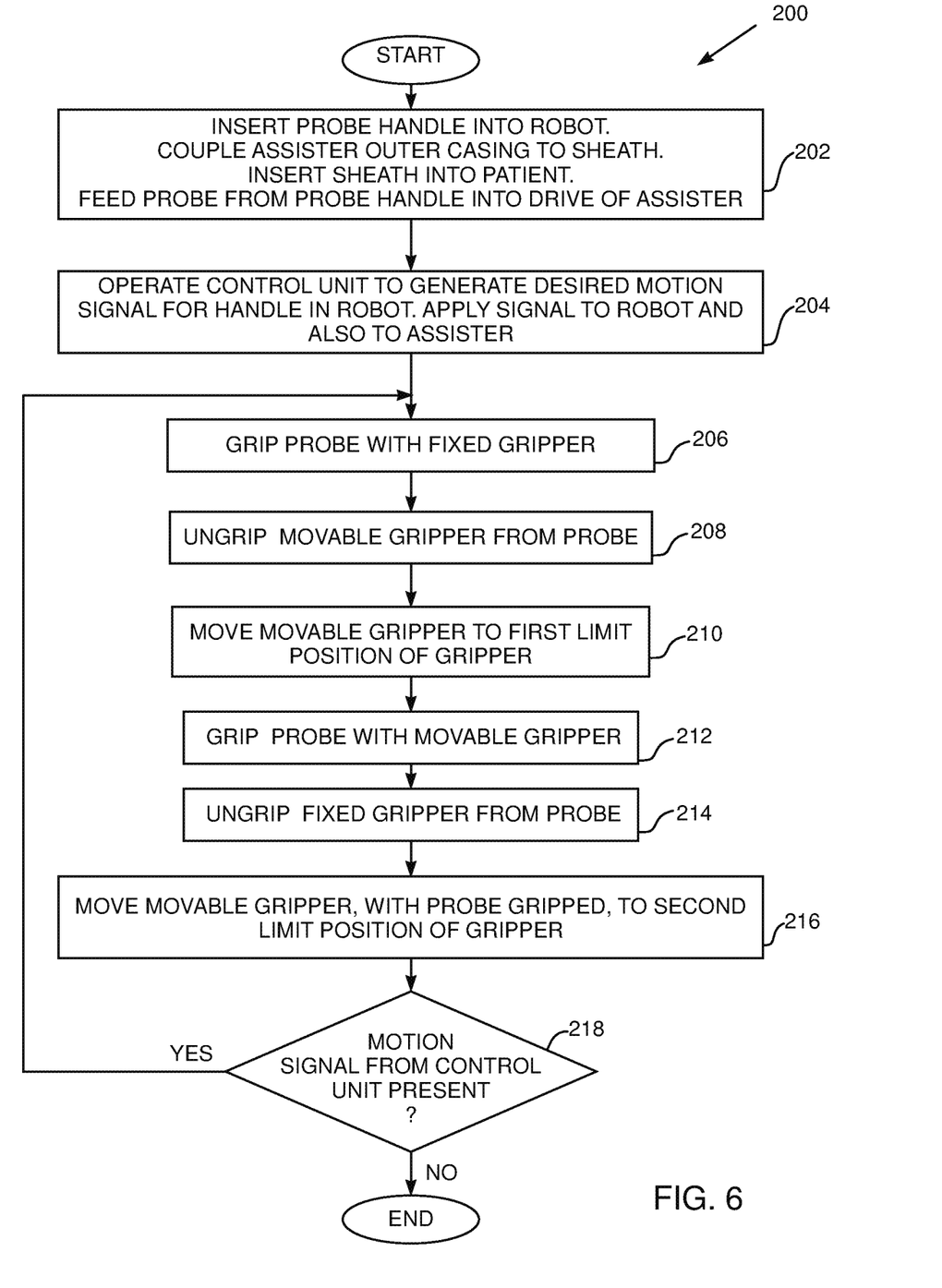
FIG. 6 is a flowchart showing steps in implementing a stepwise motion of a catheter with respect to a sheath, according to an embodiment of the present invention.

FIG. 6 is a flowchart 200 showing steps in implementing a stepwise motion of catheter 30 with respect to sheath 24, according to an embodiment of the present invention. By way of example, and for simplicity, the description of the flowchart assumes that translational motion of the catheter in a distal direction is to be implemented. Similar steps apply to translational proximal motion and to clockwise and counter-clockwise rotational motion, and those having ordinary skill in the art will be able to adapt the description, mutatis mutandis, for these other motions.

In a preparation step 202 handle 70 is inserted into robotic drive 54. In addition cuter casing 102 is connected to sheath 24, and the sheath is inserted into a patient. Typically, once the sheath has been inserted into the patient, the outer casing is temporarily fixed to the patient, such as by suturing. Probe 30 is then fed from the probe handle into drive module 100.

In an initial control unit step 204, the operator of system 20 activates control unit 52, so that the unit generates a signal for a desired motion, herein, as explained above, assumed to comprise a proximal translational motion for the probe. The signal is conveyed to robotic drive 54 which translates the handle proximally. The signal is also conveyed to circuitry 106 controlling drive module 100, so that the module performs iterative steps 206-218, described below. The iteration continues until control unit 52 no longer generates a signal for the desired motion.

Iterative steps 206-218 require energizing and de-energizing solenoids 122 and 124, and energizing and de-energizing coils 180, 190, and/or 192, all of which actions are performed sequentially. The currents required for the actions are generated by circuitry 106.

In a first iteration step 206, the circuitry closes taxed gripper 120, by energizing solenoids 122, so as to grip the probe.

In a second iteration step 208, the circuitry opens movable gripper 140 by de-energizing solenoids 142, so that the probe is not gripped by the movable gripper.

In a third iteration step 210 movable gripper 140 is moved, while open, to the proximal limit of its translation motion, by energizing coil 180.

In a fourth iteration step 212, the movable gripper is closed, by energizing solenoids 142, so as to grip the probe.

In a fifth iteration step 214, fixed gripper 120 is opened, by de-energizing solenoids 122, so as to no longer grip the probe.

The above iteration steps move the movable gripper into its required position, while maintaining the probe in a fixed location. The following iteration step describes a stepped motion of the probe.

In a sixth iteration step 216, the movable gripper is moved, while gripping the probe, to the distal of its translation motion, by energizing coil 180.

In a decision step 218, circuitry 106 checks if a motion signal is still being received from control unit 52. If the signal is being received, the stepwise motion generated by drive module 100 reiterates, by steps 206-216 being repeated. If a motion signal is no longer received, then the stepwise motion generated by the drive module terminates and the flowchart ends.

Figure 7:
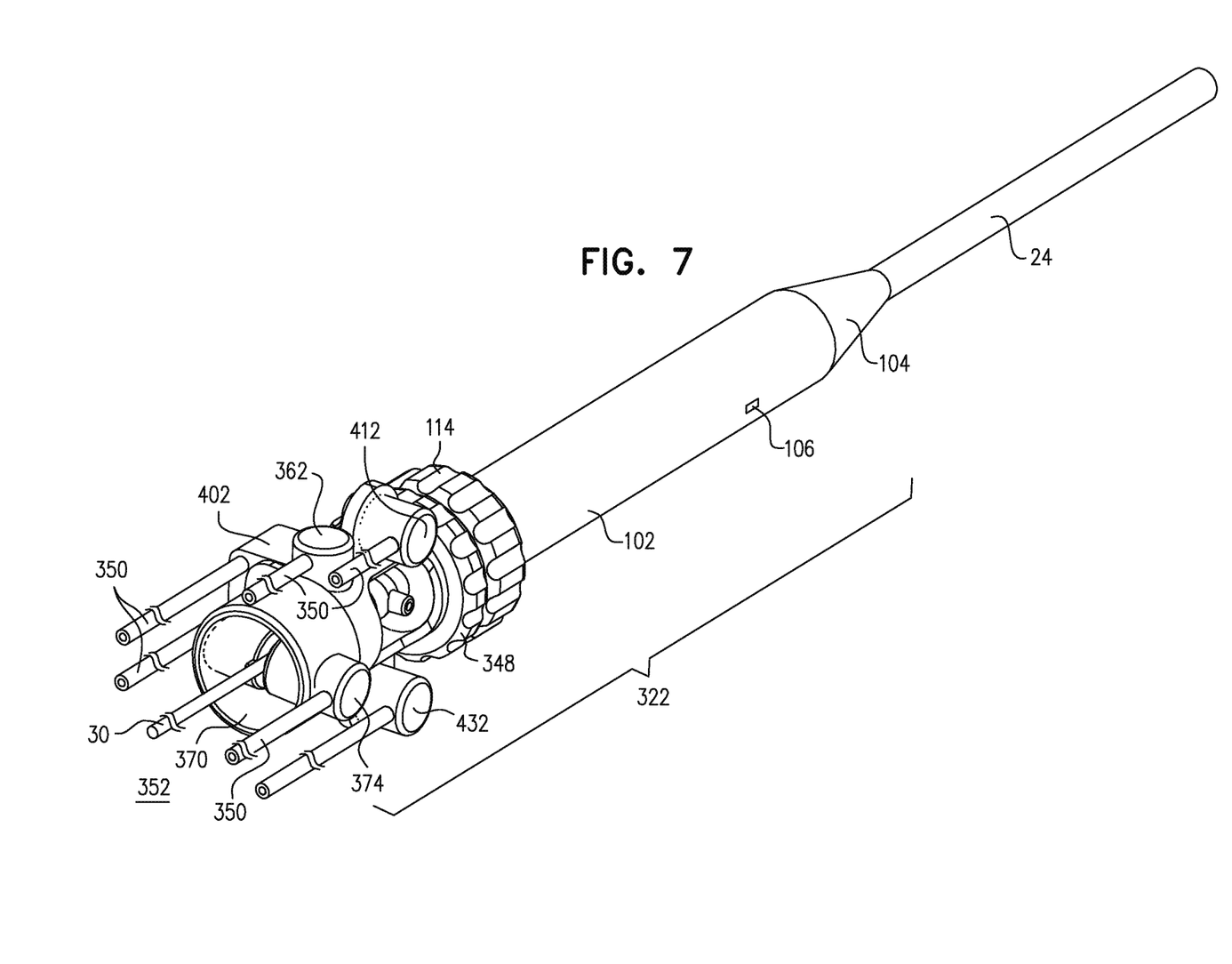
FIG. 7 is a schematic diagram of an alternative assister in an assembled state, according to an alternative embodiment of the present invention.
Figure 8:
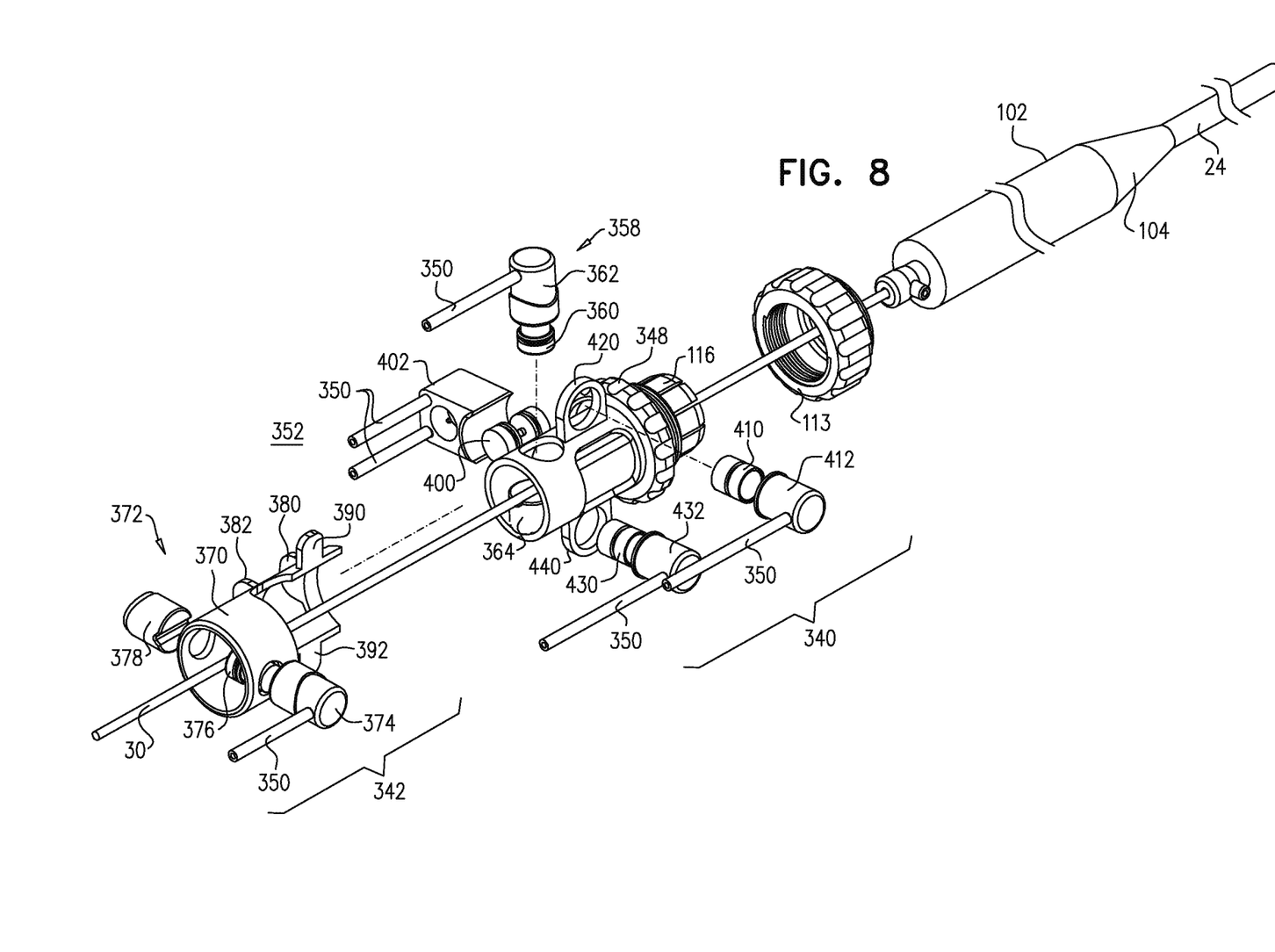
FIG. 8 is a schematic partially exploded diagram of the alternative assister, according to an alternative embodiment of the present invention.

FIG. 7 is a schematic diagram of an assister 322 in an assembled state, and FIG. 8 is a schematic partially exploded diagram of the assister, according to an alternative embodiment of the present invention. Apart from the differences described below, the operation of assister 322 is generally similar to that of assister 22 (FIGS. 1-5), and elements indicated by the same reference numerals in both assisters 22 and 322 are generally similar in construction and in operation.

In contrast to assister 22, which uses electromagnetic components for its gripper units and for its translational and rotational force generators, assister 322 uses hydraulic components for these elements. By using hydraulic components, there is no need in assister 322 for any element to be formed of magnetic materials, as are used in assister 22. Consequently, assister 322 may be used in an MRI (magnetic resonance imaging) environment, whereas use of assister 22 in such an environment may be problematic.

As for assister 22, a drive module 330 of assister 322 comprises a fixed unit 340 and a movable unit 342 which are assembled together, as illustrated in FIG. 7. As stated above, elements of assister 322 are formed with hydraulic components, which are driven by tubes 350 using a hydraulic fluid 352. Typically, the hydraulic fluid used within tubes is compressed air, which in one embodiment may be compressed to a pressure of the order of 5 or more atmospheres. However, in other embodiments fluid 352 may be air or another gas that is operated at any other convenient pressure, which may be more or less than 1 atmosphere. Alternatively, the hydraulic fluid may comprise a liquid such as water.

In fixed unit 340 a fixed base unit section 348 is locked to casing 102 using locking ring 114 and collet 116. Section 348 comprises a fixed gripper 358, consisting of a jawed piston 360 moving within a (cylinder 362, and an opposing jaw 364. When actuated by fluid 352 being applied to cylinder 362, jawed piston 360 moves within cylinder 362 so that the piston and its opposing jaw grip catheter 30.

Movable unit 342 comprises a movable unit base section 370, which in turn comprises a movable gripper 372. Movable gripper 372 consists of a cylinder 374, having a movable jawed piston 376, and an opposing jaw 378. When actuated by fluid 352 being applied to cylinder 374, jawed piston 376 moves within cylinder 374 so that the piston and its opposing jaw grip catheter 30.

Movable unit 342 comprises two translational stops: a distal translational stop 380 and a proximal translational stop 382. The movable unit also comprises two rotational stops, a first rotational stop 390, and a second rotational stop 392.

One or the other of the two translational stops may be engaged by a double-headed piston 400 moving within a piston holder 402 to which two tubes 350 are connected. Holder 402 is fixed to fixed base unit section 348. By applying fluid 352 to one of the two tubes 350 connected to holder, piston 400 moves positively in a proximal direction, contacting proximal stop 382 and causing movable unit 342 to move proximally with respect to fixed unit 340. Alternatively, fluid 352 may be applied to other tube 350 connected to holder 402, causing piston 400 to move positively in the distal direction so as to contact distal stop 380 and cause movable unit 342 to move distally with respect to fixed unit 340.

First rotational stop 390 may be engaged by a piston 410. Piston 410 moves, on application of fluid 352 to a cylinder 412, within the cylinder. Cylinder 412 is fixed, by a collar 420, to fixed base unit section 348, so that when piston 410 engages stop 390, movable unit 342 rotates in a counterclockwise direction with respect to fixed unit 340.

Second rotational stop 392 may be engaged by a piston 430. Piston 430 moves, on application of fluid 352 to a cylinder 432, within the cylinder. Cylinder 432 is fixed, by a collar 440, to fixed unit 348. Thus, when piston 430 engages stop 392, movable unit 342 rotates in a clockwise direction with respect to fixed unit 340.

Overall ranges for the translational and rotational motion of assister 322 are typically approximately the same as the respective ranges for assister 22.

Returning to FIG. 6, those having ordinary skill in the art will be able to modify the description of the steps of flowchart 200, mutatis mutandis, so that it applies to assister 322.

Embodiments of the present invention, as described above and as exemplified by assisters 22 and 322, control the motion of a catheter relative to its sheath, by assisting robotic drive 54 to overcome friction between the catheter and the sheath. In an alternative embodiment of the present invention, assister 22 or assister 322 may be configured as a force multiplier. In this case rather than robotic drive 54 applying translational and/or rotational motions to catheter 30, a human operator applies translational and/or rotational motions to the catheter, while casing 102 is fixed. The human operator may manually activate the assister to multiply the force required for the motion, i.e., a force for a proximal or distal translation, or for a clockwise or counter-clockwise rotation, according to the motion applied by the operator. Alternatively, by methods which will be familiar to those having ordinary skill in the art, the assister may be automatically activated to act as a force multiplier for the translational or rotational motions described above, according to the motion applied by the operator.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for controlling motion of an invasive probe relative to a sheath enclosing the probe, comprising:
    connecting an outer casing to the sheath;
    fixedly connecting a drive mechanism to the outer casing, wherein the outer casing extends from the drive mechanism;
    operating a first set of components in the drive mechanism to translate the probe along a direction parallel to an axis of the probe, in order to advance and retract the probe with respect to the sheath in a translational stepwise manner; and
    operating a second set of components in the drive mechanism to rotate the probe around the axis of the probe, in order to rotate the probe clockwise and counter-clockwise, with respect to the sheath, in a rotational stepwise manner.

2. The method according to claim 1, wherein the first set and the second set comprise a common sub-set of components comprising first and second grippers which releasably grip the probe in first and second positions.

3. The method according to claim 2, wherein the first gripper is fixed relative to the sheath, and wherein the second gripper is movable relative to the sheath.

4. The method according to claim 2, wherein the first gripper grips the probe while the second gripper releases the probe and while the first gripper implements one of translation and rotation of the probe.

5. The method according to claim 1, wherein the components comprise hydraulic components.

6. The method according to claim 1, wherein the components comprise electromagnetic components.

7. The method according to claim 6, and comprising supplying currents to the electromagnetic components on receipt of a control signal.

8. The method according to claim 1, wherein the first set comprises a coil and a magnet configured, on energization of the coil, to implement one of advancement and retraction of the probe.

9. The method according to claim 1, and comprising configuring solenoids to open and close first and second grippers in alternation so as to implement one of the translational stepwise manner of translation and the rotational stepwise manner of rotation.

10. The method according to claim 1, wherein the second set comprises a coil and a magnet configured, on energization of the coil, to implement one of a clockwise and a counter-clockwise rotation of the probe.

11. The method according to claim 1, and comprising using the invasive probe in an invasive procedure on a heart of a subject.

12. The method according to claim 1, wherein controlling the motion comprises multiplying a force applied to the invasive probe.

13. The method according to claim 1, wherein controlling the motion comprises overcoming friction between the sheath and the invasive probe.

* * * * *